(12) United States Patent
Fisker et al.

(10) Patent No.: US 11,553,985 B2
(45) Date of Patent: Jan. 17, 2023

(54) DRILL GUIDE ASSEMBLY

(71) Applicant: 3Shape A/S, Copenhagen (DK)

(72) Inventors: Rune Fisker, Virum (DK); Birk Ploennigs, Frederiksberg (DK); Thomas Hedegaard, Copenhagen (DK)

(73) Assignee: 3SHAPE A/S, Copenhagen K (DK)

( * ) Notice: Subject to any disclaimer, the term of this patent is extended or adjusted under 35 U.S.C. 154(b) by 146 days.

(21) Appl. No.: 15/328,643

(22) PCT Filed: Jul. 6, 2015

(86) PCT No.: PCT/EP2015/065340
§ 371 (c)(1),
(2) Date: Jan. 24, 2017

(87) PCT Pub. No.: WO2016/012223
PCT Pub. Date: Jan. 28, 2016

(65) Prior Publication Data
US 2017/0209235 A1    Jul. 27, 2017

(30) Foreign Application Priority Data
Jul. 25, 2014   (DK) .............................. PA201470462

(51) Int. Cl.
*A61C 1/08* (2006.01)
*A61C 1/00* (2006.01)
(Continued)

(52) U.S. Cl.
CPC ............ *A61C 1/084* (2013.01); *A61B 17/176* (2013.01); *A61B 34/10* (2016.02); *A61C 1/0084* (2013.01);
(Continued)

(58) Field of Classification Search
CPC . A61B 17/176; A61B 34/10; A61B 2034/108; A61C 1/084; A61C 1/085; A61C 1/0084
See application file for complete search history.

(56) References Cited

U.S. PATENT DOCUMENTS

| 5,133,660 A | 7/1992 | Fenick |
| 7,329,122 B1 * | 2/2008 | Scott ...................... A61C 1/084 |
| | | 433/18 |

(Continued)

FOREIGN PATENT DOCUMENTS

| EP | 1 894 539 A1 | 3/2008 |
| GB | 2 495 730 A | 4/2013 |

(Continued)

OTHER PUBLICATIONS

International Search Report (PCT/ISA/210) dated Sep. 10, 2015, by the European Patent Office as the International Searching Authority for International Application No. PCT/EP2015/065340.
(Continued)

*Primary Examiner* — Nicholas D Lucchesi
*Assistant Examiner* — Hao D Mai
(74) *Attorney, Agent, or Firm* — Buchanan Ingersoll & Rooney P.C.

(57) ABSTRACT

A drill guide assembly used to guide a drill into the jawbone of a patient during dental surgery includes at least one through going guide bore for guiding the drill, at least one attachment for securing a part of the drill guide assembly to the jaw of the patient during surgery, wherein the drill guide assembly includes a first part including the at least one first through going guide bore, the at least one first attachment and at least a first reference area for referring the first part to a first anatomical feature of the patient, a second part including a second reference area for referring the second part to a second anatomical feature of the patient, and a (Continued)

guiding structure for guiding the first part and the second into a desired configuration.

7 Claims, 4 Drawing Sheets

(51) Int. Cl.
*A61B 34/10* (2016.01)
*A61B 17/17* (2006.01)

(52) U.S. Cl.
CPC ........ *A61C 1/085* (2013.01); *A61B 2034/108* (2016.02)

(56) References Cited

U.S. PATENT DOCUMENTS

| | | | | |
|---|---|---|---|---|
| 8,348,669 | B1* | 1/2013 | Schmitt | A61C 9/0046 |
| | | | | 433/196 |
| 8,529,255 | B2* | 9/2013 | Poirier | A61C 1/084 |
| | | | | 433/72 |
| 8,920,167 | B2* | 12/2014 | Akutsu | A61C 1/084 |
| | | | | 433/72 |
| 9,168,112 | B2* | 10/2015 | Haber | A61C 8/0089 |
| 9,687,327 | B2* | 6/2017 | Prestipino | A61C 13/34 |
| 2003/0044749 | A1* | 3/2003 | Marotta | A61C 1/084 |
| | | | | 433/45 |
| 2006/0257817 | A1* | 11/2006 | Shelton | A61C 1/084 |
| | | | | 433/75 |
| 2008/0085489 | A1* | 4/2008 | Schmitt | A61C 1/084 |
| | | | | 433/75 |
| 2009/0239197 | A1* | 9/2009 | Brajnovic | A61C 1/084 |
| | | | | 433/174 |
| 2009/0263764 | A1* | 10/2009 | Berckmans, III | A61C 1/084 |
| | | | | 433/215 |
| 2010/0183998 | A1* | 7/2010 | Poirier | A61C 1/084 |
| | | | | 433/72 |
| 2010/0203479 | A1 | 8/2010 | Bulloch et al. | |
| 2011/0060558 | A1* | 3/2011 | Pettersson | A61B 17/8685 |
| | | | | 703/1 |
| 2011/0111362 | A1 | 5/2011 | Haber | |
| 2011/0207084 | A1* | 8/2011 | Kaigler, Sr. | A61B 17/663 |
| | | | | 433/174 |
| 2011/0311941 | A1* | 12/2011 | Yi | A61B 17/176 |
| | | | | 433/75 |
| 2012/0046914 | A1* | 2/2012 | Gao | A61C 1/084 |
| | | | | 703/1 |
| 2013/0071811 | A1 | 3/2013 | Groscurth et al. | |
| 2014/0272779 | A1* | 9/2014 | Okay | A61C 13/0004 |
| | | | | 433/75 |
| 2015/0272705 | A1* | 10/2015 | Watson | A61C 1/084 |
| | | | | 433/173 |

FOREIGN PATENT DOCUMENTS

| | | |
|---|---|---|
| WO | WO 03/071972 A1 | 9/2003 |
| WO | WO 2010/076943 A1 | 7/2010 |

OTHER PUBLICATIONS

Written Opinion (PCT/ISA/237) dated Sep. 10, 2015, by the European Patent Office as the International Searching Authority for International Application No. PCT/EP2015/065340.

\* cited by examiner

DRILL GUIDE ASSEMBLY

FIELD OF THE INVENTION

This invention generally relates to a drill guide assembly split into parts in order to facilitate access to the oral cavity during surgery and improve precision when placing the drill guide on the jaw. More particularly, the invention relates to a drill guide assembly and a method for designing a drill guide assembly.

BACKGROUND OF THE INVENTION

When performing dental implant surgery it is critical that the implant is placed correctly. This is necessary both to ensure that the restoration such as crown or denture can be placed in the correct position but also in order to ensure that the implant is anchored firmly and at the correct location in the bone structure of the jaw. Moreover, it is critical that nerves and arteries are not penetrated which can cause irrevocable damage to the patient.

In order to aid the surgeon drill guides have been produced with through going bores that guides the drill into the jawbone at the correct location and orientation. After the hole is provided an implant can be inserted whereon a restoration such as a crown, bridge or denture can be fixed.

These drill guides can be placed in different ways. Some are provided with reference areas that correspond to one or more dental feature in the jaw of the patient that allows for some precision during placement of the drill guide in the mouth.

However, there exists a need to be able to place drill guides at an even higher precision than done before. Moreover, there also exists a need to provide better access to the oral cavity in order to give the surgeon more room to operate instruments during surgery.

SUMMARY

Disclosed is a drill guide assembly used to guide a drill into the jawbone of a patient during dental surgery, the drill guide assembly comprises
 a first part comprising at least one first through going guide bore and at least a first reference area for referring the first part to a first anatomical feature of the patient,
 a second part comprising a second reference area for referring the second part to a second anatomical feature of the patient, and
 a guiding structure for guiding the first part and the second into a desired configuration.

This advantageously increases the precision at which an implant can be placed in the jaw of the patient.

In particular as the second part has a reference area that aids it into place the guiding structure will subsequently ensure that the desired configuration between the mandible and maxilla of the patient is obtained as the first and second part are moved together.

In order to ensure that the first part remains correctly in place after initial placement the drill guide assembly may in a further embodiment comprise at least one first attachment means on the first part for securing the first part of the drill guide assembly to the jaw of the patient during surgery.

In one embodiment the guiding structure comprises a first guide element provided on the first part shaped to engage with a second guide element on the second part.

This can for example be in an embodiment wherein the first guide element is geometrically shaped and the second guide element has a complementary geometrical shape. This advantageously provided guiding element that guides the first and second part into the desired configuration.

The geometrical shapes can be simply geometries such as pyramids, cones, trapezoid and similar.

In another embodiment the first guide element represent at least one tooth in one of the jaws of the patient and the second guide element represent at least one antagonist to the at least one tooth. By using the teeth shapes, such as representation of the actual teeth present in the mouth of the patient or the dental situation before surgery it is possible to maintain the occlusion of the patient as the teeth representations will guide the jaws into the desired configuration which for example is the static occlusion which the patient had before surgery.

In another embodiment the first part is split into a drill part comprising the at least one first through going bore, the at least one first attachment means and the first reference area and an intermediate part comprising at least part of the guiding structure. This is advantageously as the intermediate part can be removed and discarded before drilling, which provides more room for the patient during surgery.

In another embodiment the second part comprises at least one second though going guide bore and at least one second attachment means. In this way both the first part and the second part functions as drill guides for guiding the drill and placement of drill guides in both the maxilla and the mandible can be done in one step when implants are to be performed in both jaws.

In another aspect there is disclosed a drill guide assembly used to guide a drill into the jawbone of a patient during dental surgery, the drill guide assembly comprises
 at least one through going guide bore for guiding the drill, and
 at least one attachment means for securing a part of the drill guide assembly to the jaw of the patient during surgery,
 wherein the drill guide assembly is split into at least
 a drill part comprising the at least one first through going bore, the at least one first attachment means and at least a first reference area for referring the drill guide assembly to a first anatomical feature of the patient,
 an intermediate part comprising a guiding structure for guiding the drill guide assembly into a desired configuration relative to the jawbone of the patient.

This advantageously allows for more space during drilling as the intermediate part may be removed after the drill guide assembly has been placed.

In particular this can be understood as the guiding structure provided on the intermediate part is used for aiding in placing the drill guide assembly. After placement, the guiding structure is no longer necessary and the intermediate part, and thus also the guiding structure, is removed to provide additional space for drilling.

In order to ensure that the first part remains correctly in place after initial placement the drill guide assembly may in a further embodiment comprise at least one first attachment means on the drill part for securing the drill part of the drill guide assembly to the jaw of the patient during surgery.

In order to ensure that the drill part and the intermediate part are coupled correctly and securely together there may in one embodiment be provided a drill guide assembly, wherein the drill part and the intermediate part comprises a coupling structure for a coupling the drill part and the intermediate part in a coupling arrangement. In particular where a specific coupling arrangement is desired, i.e. the relative position between the drill part and the intermediate part is unique, the provision of coupling structures are highly advantageous.

Coupling structures that are particularly advantageous and that can be used separately or in combination can for example be a coupling structure comprising an at least partly convex surface on the drill part and a corresponding at least partly concave surface on the intermediate part, and/or an coupling structure comprising a least one protrusion on the drill part and at least one corresponding recess or opening on the intermediate part for receiving the at least one protrusion.

As discussed previously, in one embodiment the drill guide assembly may further comprise a second part comprising a second reference area for referring the second part to a second anatomical feature of the patient, and a guiding structure for guiding the drill part and the intermediate part into a desired configuration with the second part.

This advantageously increases the precision at which an implant can be placed in the jaw of the patient.

In a further aspect there is disclosed a computer implemented method for designing a drill guide assembly used to guide a drill into the jawbone of a patient during dental surgery, wherein the method comprises, obtaining a digital model of a first jaw and a second jaw of the patient in relation to each other in a desired configuration, where the first jaw represents the maxilla and the second jaw represents the mandible or vice versa, digitally designing a first part of the drill guide assembly comprising at least one first through going guide bore for guiding a drill and design a first reference area corresponding to the topography of at least a part of the first jaw, digitally designing a second part of the drill guide assembly comprising a second reference area corresponding to the topography of at least a part of the second jaw, digitally providing a guiding structure for guiding the first and second part into the desired configuration.

In one embodiment, the computer implemented method further comprises digitally designing at least one first attachment means on the first part for securing the first part of the drill guide assembly to the first jaw.

In one embodiment the computer implemented method comprises digitally designing the guiding structure comprising an intermediate part provided between the first and second part and comprising intermediate guiding elements for engaging with first guiding elements designed on the first part and second guiding element provided on the second part.

In another embodiment the step of designing the second part further comprises designing at least one second through going bore and at least one second attachment means.

In another embodiment the step of digitally providing the guiding structure comprises on the first and second part respectively comprises digitally designing a first guide element on the first part shaped to engage with a second guide element on the second part.

Different features and embodiments can be applied for the computer implemented method.

In one embodiment the digital model comprises a CT scan and an optical surface scan. Based on this the design through going guide bore can be based on the planned implant position planned from CT scan.

Different types of anatomical features can be used as reference areas of the first and second part. Such features can for example be the palatal area, teeth, jawbone or gum/gingiva.

The desired configuration may be set as being the static occlusion of the patient before surgery, this can for example be derived from teeth existing before surgery or from an existing denture. Alternatively, the desired configuration may be determined by analyzing the bite of the patient, for example in an articulator. In particular, the desired configuration may be determined digitally, for example by performing an analysis in a virtual articulator or other digital jaw motion simulation software. This can for example be desirable in order to correct for malocclusion or TMJ (temporal mandibular joint) disorders.

During digital design of the drill guide assembly different design guides and references can be used. This can for example be the estimated or determined occlusal plane, a midline, pupillary line or other relevant reference.

The digitally designed drill guide assembly can be manufactured using well known CAD/CAM manufacturing processes, such as 3D printing and milling.

In yet a further aspect there is disclosed a computer implemented method for designing a drill guide assembly used to guide a drill into the jawbone of a patient during dental surgery, wherein the method comprises, obtaining a digital model of a first jaw and a second jaw of the patient in relation to each other in a desired configuration, where the first jaw represents the maxilla and the second jaw represents the mandible or vice versa, digitally designing a drill part of the drill guide assembly comprising at least one first through going bore and at least a first reference area corresponding to the topography of at least a part of the first jaw, and digitally designing an intermediate part of the drill guide assembly comprising a guiding structure for guiding the drill guide assembly into a desired configuration relative to the first and second jaw of the patient.

In one embodiment, the computer implemented method further comprises digitally designing at least one first attachment means on the drill part for securing the drill part of the drill guide assembly to the first jaw.

Different features and embodiments can be applied for the computer implemented method.

In one embodiment the digital model comprises a CT scan and an optical surface scan. Based on this the design through going guide bore can be based on the planned implant position planned from CT scan.

Different types of anatomical features can be used as reference areas of the drill part. Such features can for example be the palatal area, teeth, jawbone or gum/gingiva.

The desired configuration may be set as being the static occlusion of the patient before surgery, this can for example be derived from teeth existing before surgery or from an existing denture. Alternatively, the desired configuration may be determined by analyzing the bite of the patient, for example in an articulator. In particular, the desired configuration may be determined digitally, for example by performing an analysis in a virtual articulator or other digital jaw motion simulation software. This can for example be desirable in order to correct for malocclusion or TMJ (temporal mandibular joint) disorders.

During digital design of the drill guide assembly different design guides and references can be used. This can for example be the estimated or determined occlusal plane, a midline, pupillary line or other relevant reference.

The digitally designed drill guide assembly can be manufactured using well known CAD/CAM manufacturing processes, such as 3D printing and milling.

In one aspect there is disclosed a computer program software, that when executed on a computer controlled device enables a user to perform the steps of the computer implement methods disclosed herein.

In one aspect there is disclosed a computer controlled device, comprising
- a digital storage memory for storing the computer program software as disclosed herein,
- a processing unit for executing the computer program software based on input from an user,
- an input device through which the user can provide input to the processing unit, and
- an output device for relaying information from the processing unit to the user.

In one aspect there is disclosed a use of a drill guide assembly as described herein for guiding drilling in a patient's jawbone.

In one aspect there is disclosed a method for designing a drill guide assembly used to guide a drill into the jawbone of a patient during dental surgery.

The method may comprise the steps disclosed in the computer implemented method described herein.

In one embodiment the method comprises scanning a denture and uses the digital representation of the denture as a basis for digitally designing the drill guide assembly.

BRIEF DESCRIPTION OF THE DRAWINGS

The above and/or additional objects, features and advantages of the present invention, will be further described by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced.

Figure 1:
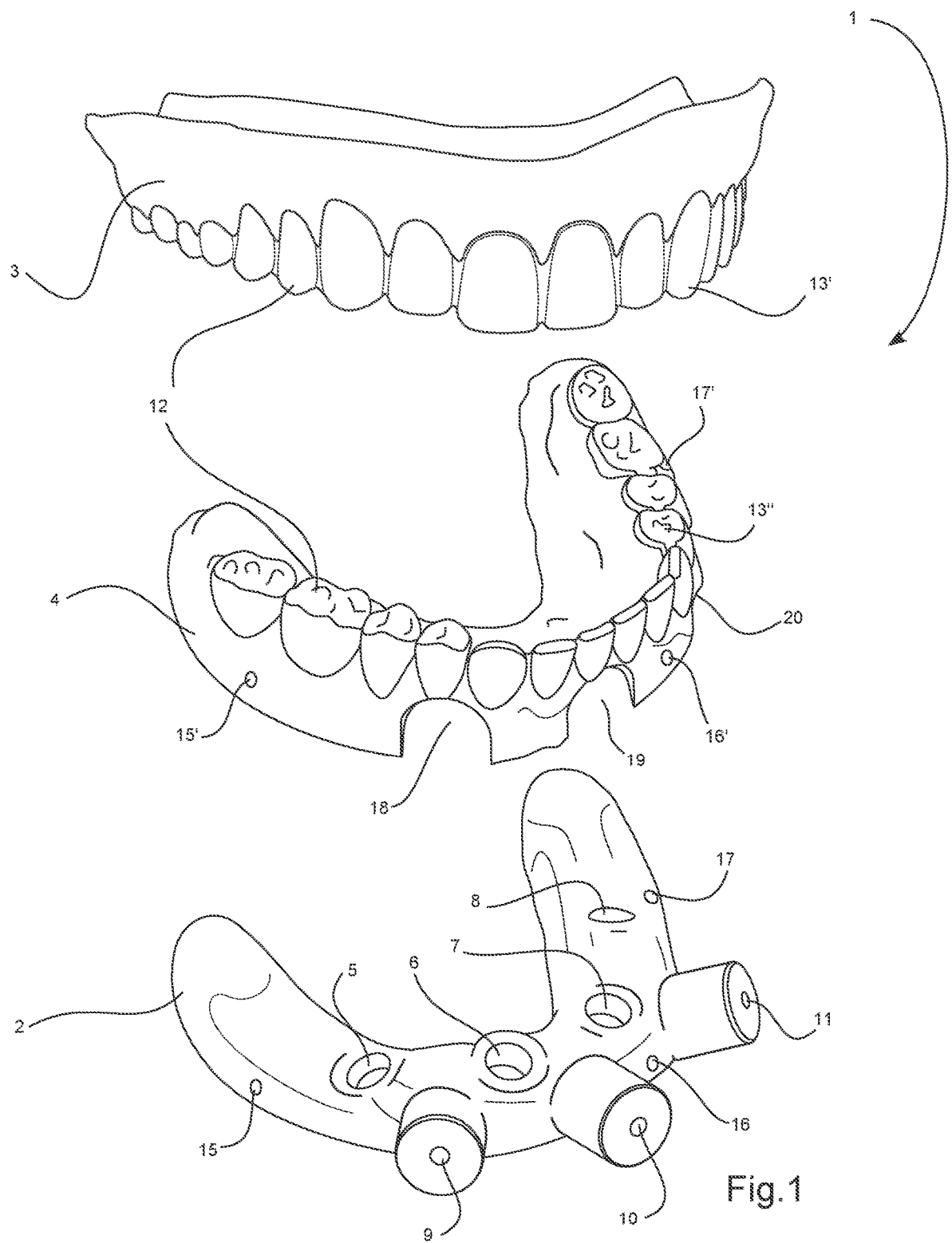
FIG. 1 shows one embodiment of a drill guide assembly according to the invention.

FIG. 1 shows one embodiment of a drill guide assembly 1 comprising a first part comprising a drill guide 2 and an intermediate part 4 and a second part 3.

The drill guide 2 comprises four through going guide bores 5, 6, 7, 8 that are provide for guiding a drill during surgery. In order to retain the drill guide so that it does not move during surgery there are provided attachment means in the shape of three through going attachment bores 9, 10, 11 through which screws can be inserted into the jaw bone. Drill guides are in general used today and serve mainly to guide the surgeon during drilling. However, although the gum facing surface of the drill guide (not seen in the figure) is shaped to fit the gum surface as a first reference area this is not always enough to ensure correct placement of the drill guide on the jaw of the patient.

In order to ensure better alignment a guiding structure 12 is provided as guiding elements in the shape of teeth representations 13', 13" on the second part and on the intermediate part respectively. The teeth representations are based on the patient's prior dental setup, for example natural teeth that was removed before surgery or a denture, which is scanned in order to provide a digital representation of the dental setup. Accordingly, the teeth representations 13',13" will guide the second part and the intermediate part into a desired configuration that in the current embodiment corresponds to the static occlusion of the patient prior to surgery.

The intermediate part and the drill guide are adapted to be coupled together in a fixed relationship that can be separated when desired. In the current embodiment a part of the intermediate part is designed to match a part of the drill guide and three screw bores 15, 15', 16, 16', 17, 17' are provide on the drill guide and the intermediate part respectively for maintaining the parts in a fixed relationship by inserting screws through the respective bores.

When drilling is to be done the drill guide assembly 1 is inserted in the jaw of the patient with the drill guide and the intermediate part fixed together by screws via the screw bores 15, 15', 16, 16', 17, 17'. The patient is then asked to bite down. This causes the first reference area (not shown) of the drill guide aligns with a corresponding area of the gum of the mandible and the second reference area (not shown) of the second part aligns with a corresponding area of the gum of the maxilla. At the same time the guiding elements in the form of teeth representations 13' and 13" aligns the second part with the intermediate part.

While the patient bites down the first part is attached to the mandible by using attachment screws that are screwed through the through going attachment bores 9, 10, 11 and into the jaw bone. With the first part attached the second part can be removed. The screws are then removed from the screw bores and the intermediate part can be removed from the drill guide. Slots 18, 19 and 20 allows for the through going attachment bores to slide by while removing the intermediate part.

Accordingly, only the drill guide remains which can be designed as small as possible allowing for optimised access for the surgeon during drilling.

Figure 2A:
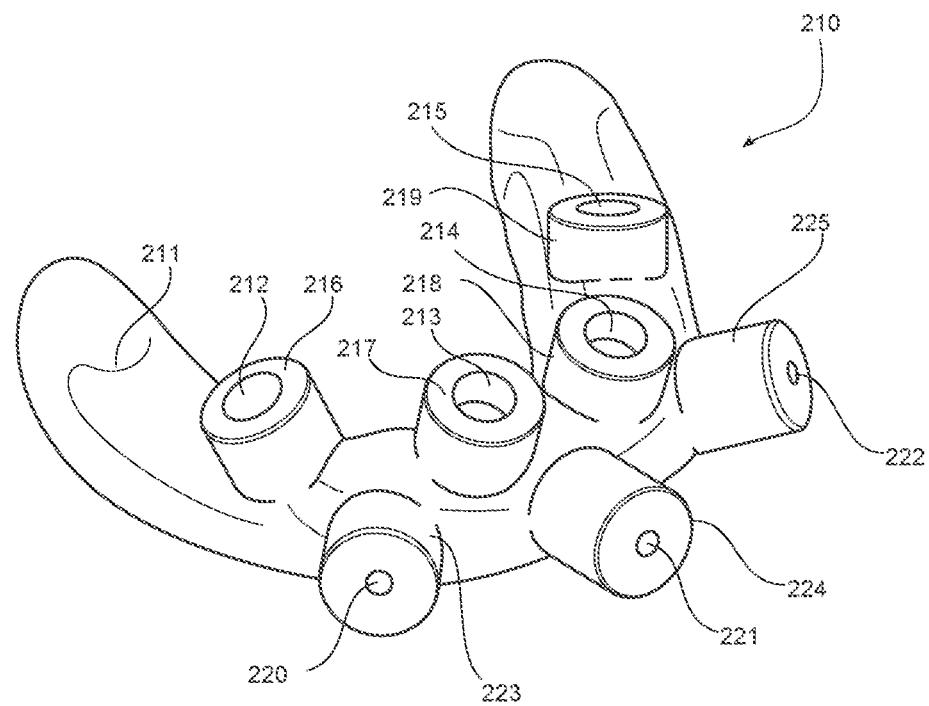
FIGS. 2a-2c shows one embodiment of a drill guide assembly according to one aspect of the invention.
Figure 2B:
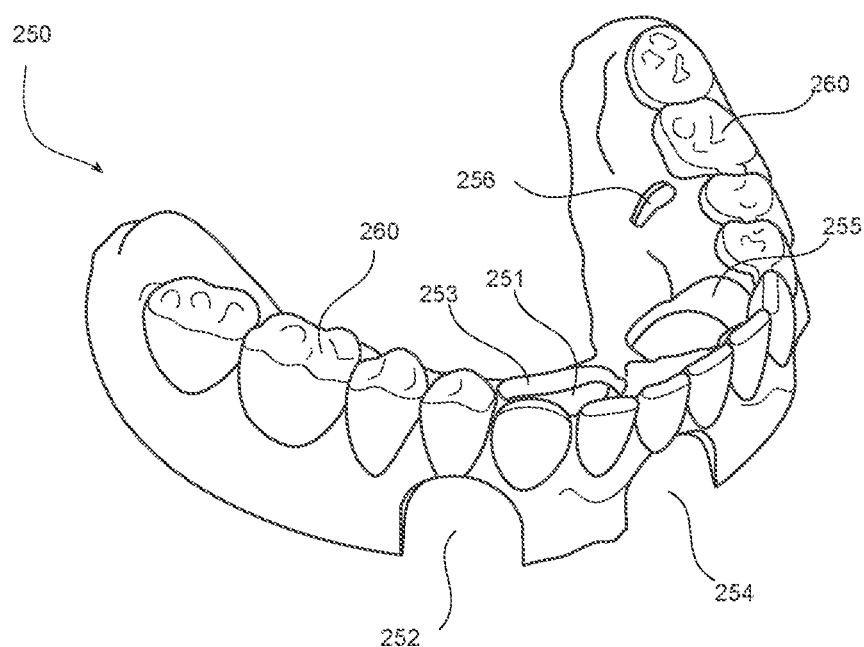
Figure 2C:
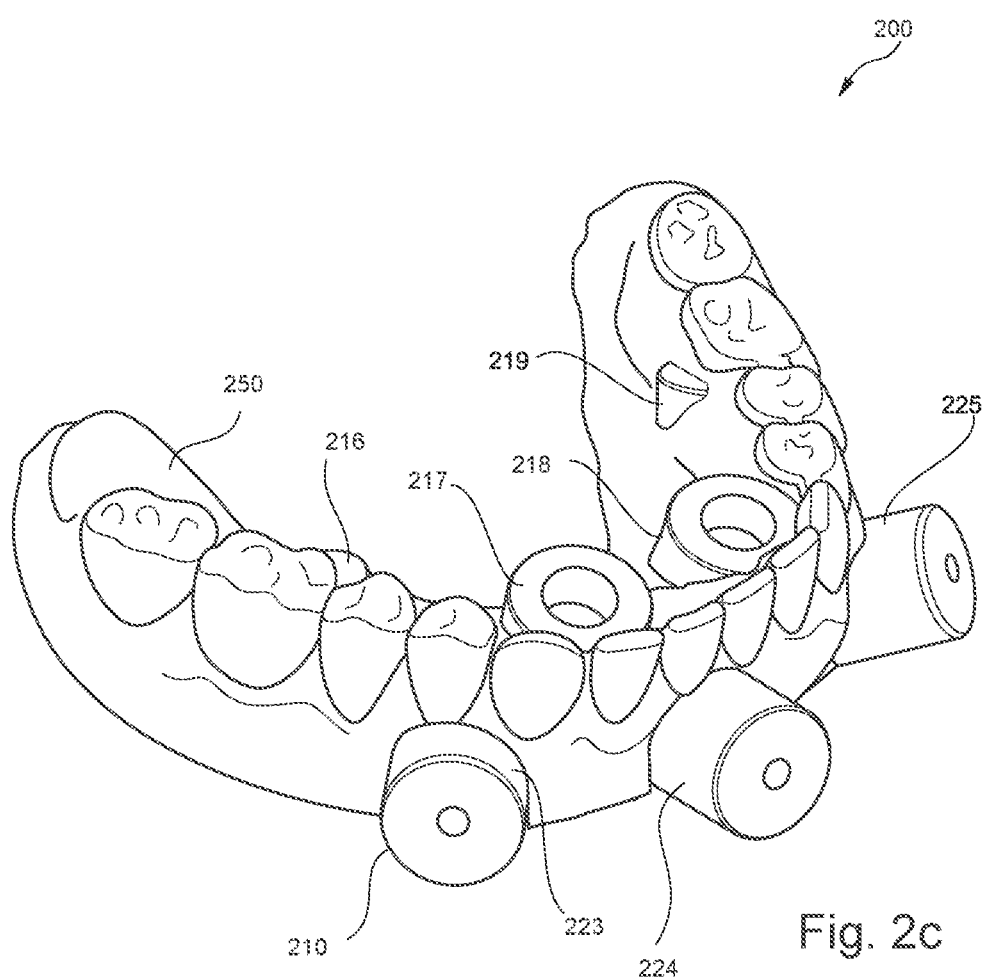

A second embodiment of one aspect of the invention is shown in FIGS. 2a-2c wherein a guide part 210 an intermediate part 250 is provided and coupled together in a drill guide assembly 200. The guide part 210 is formed with a proximal gingiva facing surface (not visible in the image) which during the digital design steps where shaped to fit the gum surface of the patient. A distal coupling surface 211 was formed digitally by offsetting the proximal gingiva facing surface.

Four through going guide bores 212, 213, 214, 215 extends through the drill part from the proximal gingiva facing surface and respective coaxially aligned guide cylinders 216, 217, 218, 219 which extends out from the distal coupling surface. The guide bores aids the drill doing drilling and the guide cylinders provide added support to the drill in order to guide it at the proper angle when drilling.

In addition there is provided three through going attachment bores 220,221,222 that extend through the drill part from the proximal gingiva facing surface and out through respective coaxially aligned attachment cylinders 223, 224, 225 which extend out from the distal coupling surface. The attachment bores allows for attachment of the drill part to the jawbone as attachment screws (not shown) can be screwed through the attachment bores into the jaw bone. The attachment cylinders provides for added material which the guide and secures the attachment screws.

The intermediate part 250 is formed with a proximal drill part facing surface 251 (only partly visible in the figures). The proximal drill part facing surface has a shape and topography that corresponds to the distal coupling surface of the drill part. This allows the drill part and intermediate part to fit snugly together.

Furthermore the intermediate part is provided with recesses and cut-outs 252, 253, 254, 255, 256 for receiving guide and attachment cylinders 223, 217,224, 218, 225, 219 (the cut-out for receiving guide cylinder 216 is not visible in the figures). First of all this provides room for the cylinders so that the drill part and intermediate part can be coupled into a drill guide assembly. However, it also functions as a further coupling structure ensuring that the drill guide assembly 200 is retained in the desired coupling arrangement.

A distal guiding surface is provided on the intermediate part whereon guide structures are provided in the shape of teeth representations 260. The teeth representations are designed to engage with an opposing dental setup, e.g. an opposing denture or opposing natural teeth. This ensures that the drill guide assemble is correctly placed before it is attached to the jawbone via the attachment bores.

Figure 3:
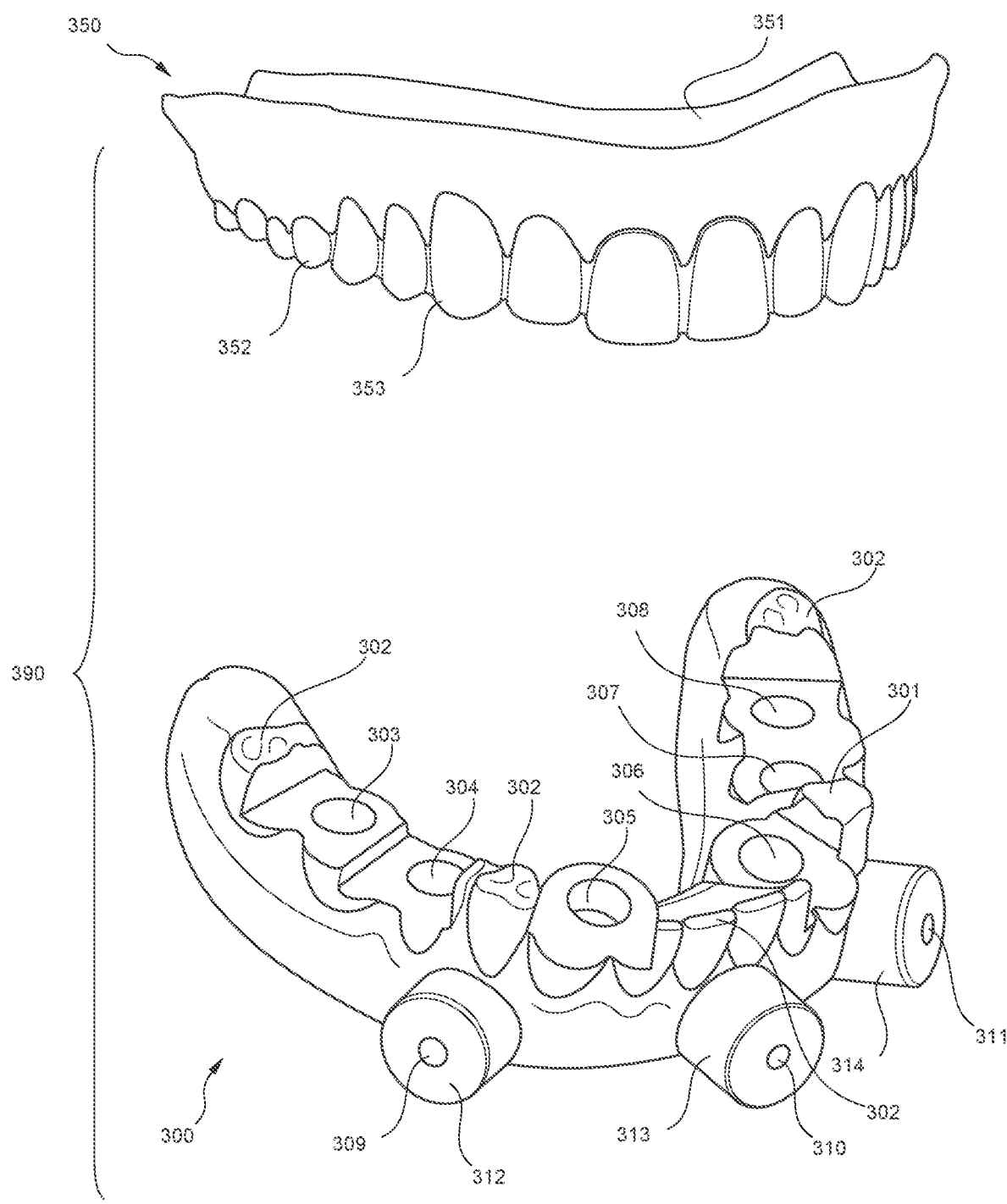
FIG. 3 shows one embodiment of a drill guide assembly according to another aspect of the invention.

A third embodiment of another aspect of the invention is shown in FIG. 3, wherein a drill guide assembly 390 is formed of a first part 300 and a second part 350.

The first part is formed with a proximal gingiva facing surface (not visible in the surface) which is adapted to fit the gingiva. A distal guiding surface 301 faces opposite the proximal gingiva facing surface whereon guiding structures in the shape of mandible teeth representations 302 have been provided.

Through going guide bores 303, 304, 305, 306, 307, 308 are provided that extends through the first part from the proximal gingiva facing surface to the distal guiding surface. As described previously, such guide bores are used to guide the drill during drilling of implant bores in the jawbone.

Attachment bores 309, 310, 311 are also provided in the first part and extend from the proximal gingiva facing surface through to the distal guiding surface. Attachment cylinders 312, 313, 314 are formed on the distal guiding surface extending coaxially with the respective attachment bores. The attachment bores are used for guiding attachment screws (not shown) in order to attach the first part to the jaw bone.

The second part is formed with a second proximal gingiva surface 351 and an oppositely facing second distal guiding surface 352. On the second distal guiding surface there are formed guiding structures in the shape of teeth representations 353.

Thus, during use the drill guide assembly 390 is arranged in the edentulous patient so that the first part 300 is placed on the gum surface of mandible and the second part is placed on the gum surface of the maxilla. The patient is then asked to bite down, or the jaws are pressed together manually. The guiding structures 302 and 352 engage each other and via the gingiva facing surfaces the drill guide assembly is guided into its optimal position. With the patient still biting down the first part is secured to the jawbone of the mandible via the attachment bores. The second part can then be removed and drilling can be initiated through the guide bores.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

The invention claimed is:

1. A drill guide assembly for guiding a drill into a jawbone of a patient during dental surgery, wherein the drill guide assembly comprises, as separate parts, at least:
    a drill part comprising at least one first through going bore for guiding a drill, a first matching part, and at least a first reference area for referring the drill guide assembly to a first anatomical feature in a form of a first jaw of the patient,
    an intermediate part comprising a second matching part and a first guiding structure, wherein the first and second matching parts comprise corresponding bores that are configured to align and allow coupling of the drill part with the intermediate part for fixedly holding the drill part and the intermediate part in a fixed relationship with the first anatomical feature, and
    a second part comprising a second reference area for referring the second part to a second anatomical feature in a form of a second jaw of the patient, and a second guiding structure for guiding the drill part and the intermediate part into a desired configuration with the second part,
    wherein the first and second guiding structures are configured to align the second part with the intermediate part when the patient bites down,
    wherein the drill part and the intermediate part comprise a coupling structure for coupling the drill part and the intermediate part in a coupling arrangement,
    wherein the coupling structure comprises a least one protrusion on the drill part and at least one corresponding recess or opening on the intermediate part for receiving the at least one protrusion,
    wherein the at least one protrusion on the drill part extends outwards and the at least one corresponding recess or opening comprises a front facing cutout section.

2. The drill guide assembly according to claim 1, wherein the drill guide assembly further comprises at least one first attachment on the drill part for securing the drill part of the drill guide assembly to the first jaw of the patient during surgery.

3. The drill guide assembly according to claim 1, wherein:
    the first guiding structure of the intermediate part comprises a first guiding element in the shape of teeth representations of the first jaw of the patient, and
    the second guiding structure of the second part comprises a second guiding element in the shape of teeth representations of the second jaw of the patient.

4. The drill guide assembly according to claim 1, wherein the drill part is a unitary piece, wherein the drill part is configured to be placed directly on the first jaw.

5. A computer implemented method for designing and manufacturing a drill guide assembly used to guide a drill into a jawbone of a patient during dental surgery, wherein the method comprises:
    obtaining a digital model of a first jaw and a second jaw of the patient in relation to each other in a desired configuration, where the first jaw is the maxilla and the second jaw is the mandible, or vice versa; digitally designing the drill guide assembly based on the digital model of the first jaw and the second jaw; and manufacturing the drill guide assembly according to the digitally designed drill guide assembly;

wherein the step of digitally designing the drill guide assembly comprises:

digitally designing a drill part of the drill guide assembly, the drill part comprising at least one first through going bore for guiding a drill, a first matching part, and at least a first reference area corresponding to a topography of at least a part of the first jaw, digitally designing an intermediate part of the drill guide assembly, the intermediate part comprising a second matching part and a first guiding structure, wherein the first and second matching parts comprise corresponding bores that are configured to align and allow coupling of the drill part with the intermediate part for fixedly holding the drill part and the intermediate part in a fixed relationship with the first jaw, and digitally designing a second part of the drill guide assembly, the second part comprising a second reference area for referring the second part to the second jaw of the patient, and a second guiding structure for guiding the drill part and the intermediate part into a desired configuration with the second part, wherein the first and second guiding structures are configured to align the second part with the intermediate part when the patient bites down, wherein the drill part and the intermediate part comprise a coupling structure for coupling the drill part and the intermediate part in a coupling arrangement, wherein the coupling structure comprises a least one protrusion on the drill part and at least one corresponding recess or opening on the intermediate part for receiving the at least one protrusion, wherein the at least one protrusion on the drill part extends outwards and at least one corresponding recess or opening comprises a front facing cutout section.

6. The computer implemented method according to claim 5, further comprising digitally designing at least one first attachment on the drill part for securing the drill part of the drill guide assembly to the first jaw.

7. The computer implemented method according to claim 5, wherein the drill part is a unitary piece, wherein the drill part is configured to be placed directly on the first jaw.

* * * * *